United States Patent
Jacobson

(10) Patent No.: US 10,786,445 B2
(45) Date of Patent: *Sep. 29, 2020

(54) METHODS OF INTRAVENOUS ADMINISTRATION OF GLYBURIDE

(71) Applicant: BIOGEN CHESAPEAKE LLC, Cambridge, MA (US)

(72) Inventor: Sven Martin Jacobson, New York, NY (US)

(73) Assignee: Biogen Chesapeake LLC, Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/459,893

(22) Filed: Jul. 2, 2019

(65) Prior Publication Data

US 2019/0328653 A1 Oct. 31, 2019

Related U.S. Application Data

(63) Continuation of application No. 15/686,989, filed on Aug. 25, 2017, now Pat. No. 10,391,053, which is a continuation of application No. 15/425,874, filed on Feb. 6, 2017, now Pat. No. 10,052,280, which is a continuation of application No. 15/422,358, filed on Feb. 1, 2017, now abandoned, which is a continuation of application No. 14/878,232, filed on Oct. 8, 2015, now Pat. No. 9,561,176, which is a continuation of application No. 14/525,992, filed on Oct. 28, 2014, now Pat. No. 9,254,259, which is a continuation of application No. 13/811,037, filed as application No. PCT/US2011/044397 on Jul. 18, 2011, now Pat. No. 8,946,293.

(60) Provisional application No. 61/365,689, filed on Jul. 19, 2010.

(51) Int. Cl.
 *A61K 9/00* (2006.01)
 *A61K 31/64* (2006.01)
 *A61K 31/18* (2006.01)
 *A61K 31/17* (2006.01)

(52) U.S. Cl.
 CPC ............ *A61K 9/0019* (2013.01); *A61K 31/17* (2013.01); *A61K 31/18* (2013.01); *A61K 31/64* (2013.01)

(58) Field of Classification Search
 CPC .......... A61K 9/00; A61K 31/64; A61K 31/18; A61K 31/17
 See application file for complete search history.

(56) References Cited

U.S. PATENT DOCUMENTS

| 7,285,574 B2 | 10/2007 | Simard et al. |
| 7,872,048 B2 | 1/2011 | Simard |
| 8,136,330 B2 | 3/2012 | Ostler |

| 2004/0073192 A1 | 4/2004 | Flament-Garcia |
| 2005/0148928 A1 | 7/2005 | Molina |
| 2008/0220441 A1 | 9/2008 | Birnbaum et al. |
| 2009/0233995 A1 | 9/2009 | Lautt |

FOREIGN PATENT DOCUMENTS

| CN | 1960735 A | 5/2007 |
| EP | 2595633 A2 | 5/2013 |
| JP | 2000/512266 A | 9/2000 |
| WO | 2005112949 A1 | 12/2005 |
| WO | 2006036278 A2 | 4/2006 |
| WO | 2008038126 A2 | 4/2008 |
| WO | 2009002832 A2 | 12/2008 |
| WO | 2009097443 A2 | 8/2009 |
| WO | 2012012347 A2 | 1/2012 |

OTHER PUBLICATIONS

Garrell et al.; Acute Effect of Glyburide on Insulin Sensitivity in Type I Diabetic Patients; Journal of Clinical Endocrinology and Metabolism; Nov. 1, 1987; pp. 896-900; vol. 65, No. 5; The Endocrine Society; US.
Jonsson et al.; Effects and pharmacokinetics of oral glibenclamide and glipizide in Caucasian and Chinese patients with type-2 diabetes; European Journal of Clinical Pharmacology; Dec. 1, 2000; pp. 711-714; vol. 56, No. 9-10; Springer-Verlag.
Jonsson et al.; Pharmacodynamics and pharmacokinetics of intravenous glibenclimide in Caucasian and Chinese patients with type-2 diabetes; European Journal of Clinical Pharmacology; Jan. 1, 2000; pp. 721-727; vol. 55, No. 10; Springer-Verlag.
Rogers, et al.; Pharmacokinetics of Intravenous Glibenclamide Investigated by a High Performance Liquid Chromatographic Assay; Diabetologia; Jul. 1, 1982; pp. 37-40; vol. 23, No. I; Springer-Verlag, Berlin, Germany.
Rydberg et al.; Concentration-effect relations of glibenclamide and its active metabolites in man: modeling of Pharmacokinetics and Pharmacodynamics; British Journal of Clinical Pharmacology; Apr. 1, 1997; pp. 373-373; Blackwell Science Ltd., England.
Sorgel et al.; Pharmacodynamics of oral and parenteral Glibenclamide; Pharmaceutical Research (supplement); Nov. 1997; pp. SI 77-SI 78; vol. 14, No. 11; (also from Annual Meeting of the American Association of Pharmaceutical Scientists; Boston Massachusetts, USA; Nov. 2-6, 1997).
Bank et al, "Vascular ATP-dependent potassium channels, nitric oxide, and human forearm reactive hyperemia." Cardiovasc. Drugs Ther., 2000, 14(1):23-29.
Bauerafelnd et al, "Comparative Bactericidal Effect of Discontinuous vs Continuous Dosing of Meropenem in a Pharmacodynamic Model", Pharmaceutical Research, 1997, pp. 3, vol. 14, No. 11, New York.

(Continued)

Primary Examiner — Shirley V Gembeh
(74) Attorney, Agent, or Firm — Rothwell, Figg, Ernst & Manbeck, P.C.

(57) ABSTRACT

The present disclosure is drawn to a method of treating a patient in need of treatment, comprising identifying a patient in need of treatment for stroke, traumatic brain injury, spinal cord injury, myocardial infarction, shock, organ ischemia, ventricular arrhythmias, ischemic injury, or hypoxia/ischemia; administering a bolus of glyburide to the patient; and administering a continuous infusion of glyburide to the patient at from about 15 µg/hr and about 300 µg/hr, wherein the continuous infusion glyburide is administered for a period of time more than about 20 hours.

20 Claims, 5 Drawing Sheets

(56) References Cited

OTHER PUBLICATIONS

Billman et al, "The Effects of the ATP-Dependent Potassium Channel Antagonist, Glyburide, on Coronary Blood Flow and Susceptibility to Ventricular Fibrillation in Unanesthetized Dogs", Journal of Cardiovascular Pharmacology, Feb. 1993, pp. 10, vol. 21, No. 2, Columbus, OH.

Boggs et al, "Potential of Glyburide to Reduce Intracerebral Edema in Brain Metastases", Expert Reviews, 2014, pp. 10, vol. 14, Issue 4, Baltimore, MD.

Britton et al, "Effects of Glimepiride vs Glibenclamide on Ischaemic Heart Disease Risk Factors an Glycaemic Control in Patients with Type 2 Diabetes Mellitus", Clinical Pharmacodynamics, 1998, pp. 17, London, England.

Chatila et al, "Hepatomegaly and abnormal liver tests due to glycogenosis in adults with diabetes." Medicine (Baltimore), 75:327-333, 1996.

El-Reyani et al, "Comparison of the Efficacy of Glibenclamide and Glimepiride in Reperfusion-Induced Arrhythmias in Rats", European Journal of Pharmacology, 1999, pp. 187-192, vol. 365, Hungary.

Elrod et al, "Role of Sulfonylurea Receptor Type 1 Subunits of ATP-Sensitive Potassium Channels in Myocardial Ischemia/Reperfusion Injury", Circulation Journal of the AHA, Mar. 2008, pp. 10, Online ISSN 1524-4539, Dallas, TX.

Figura et al, "Blockade of KATP Channels Reduces Enothelial Hyperpolarization and Leukocyte Recruitment Upon Reperfusion After Hypoxia", American Journal of Transplantation, 2009, pp. 687-696, vol. 9, Alberta, Canada.

Zhou et al, "Glibenclamide Improves Neurological Function in Neonatal Hypoxia Ischemia in Rats", Brain Research, Mar. 2009, pp. 33, Loma Linda, CA.

Groop et al, "Different effects of glyburide and glipizide on insulin secretion and hepatic glucose production in normal and NIDDM subjects.", Diabet, 1987, 36:1320-1328.

Groop et al, "Dose-dependent effects of glyburide on insulin secretion and glucose uptake in humans." Diabetes Care. Aug. 1991;14(8):724-7.

Irwin et al, "Dietary wheat starch and sucrose: Effects on levels of 5 enzymes in the blood serum of young adults." Am J Clin Nutr 22, 701-9, 1969.

Iskit et al, "Glibenclamide Attenuates the Antiarrhythmic Effect ofEndotoxin with a Mechanism not Involving KATP Channels", ScienceDirect, 2006, pp. 129-136, Turkey.

Jayakumar et al, "Sulfonylurea Receptor 1 Contributes to the Astrocyte Swelling and Brain Edema in Acute Liver Failure", Springer Science, Jan. 2014, pp. 10, New York.

Jew et al, "Glibenclamide Improves Postischemic Recovery of Myocardial Contractile Function in Trained and Sedentary Rats", University of Colorado Cardiovascular Institute, May 2001, pp. 10, Boulder, CO.

Vajda et al, "Selective Cardiac Plasma-Membrane KATP, Channel Inhibition is Defibrillatory and Improves Survival During Acute Myocardial Ischemia and Reperfusion", European Journal of Pharmacology, 2007, pp. 115-123, vol. 577, Hungary.

Szabo et al, "Inhibition of ATP-Activated Potassium Channels Exerts Pressor Effects and Improves Survival in a Rat Model of Severe Hemorrhagic Shock", Shock: Rapid Communication, 1996, pp. 391-394, vol. 5 No. 6, Cincinnati, OH.

Katoh et al, "Association Between Body Composition and Glucose Intolerance in Patients with Quadriplegics", Sogo Rehabilitation, Apr. 2003, vol. 31, No. 4, Japan.

Kechagieas et al, "Fast food based hyper-alimentation can induce rapid and profound elevation in serum alanine aminotransferase in healthy subjects", Gut 57(5):649-54, 2008.

Office Action for Japanese application No. 2013-520785, dated Apr. 22, 2015.

Legtenberg et al, "Glibenclamide Attenuates Ischemia-Induced Acidosis and Loss of Cardiac Function in Rats", European Journal of Pharmacology, 2002, pp. 35-42, vol. 434, Netherlands.

Maekawa et al, "Clinical Image of Acute Myocardial Infraction as a Complication of Diabetes—Study With Respect to the Presence of Glibenclamide Dosing", Japanese Circulation Journal, Sep. 2000, pp. 2, vol. 64, Japanese Red Cross Okayama Hospital, Japan.

Mahgoub et al, "Diabetes Mellitus and Cardiac Function", Molecular and Cellular Biochemisrty, 1998, pp. 59-64, vol. 180, Richmond, VA.

Maybauer et al, "The ATP-Sensitive Potassium-Channel Inhibitor Glibenclamide Improves Outcome in an Ovine Model of Hemorrhagic Shock", University of Texas Medical Branch, Jul. 2004, pp. 387-391, vol. 22, No. 4, Texas.

McEwen et al, "Characterisation of glibenclamide half-life in man: acute concentration-effect relationships", Clinical Science, 1982, 63:28.

Morrison et al, "Effect of pirprofen on glibenclamide kinetics and response", Br. J. Clin. Pharmac, 1982, 14:123-126.

Neugebauer et al, "Absolute bioavailability and bioequivalence of glibenclamide (Semi-Euglucon N)", Int. J. Clin. Pharmacol. Ther. Toxicol, 1985, 23(9):453-60.

Oku, "Arterioslerotic Disease Management of Disease as a Complication in Stroke Rehabilitation", Gendai Iryo, Up Date, 1992, pp. 14, vol. 92, No. 24, ISSN 0533-7259, Japan.

Patel et al, "Glibenclamide Reduces Hippocampal Injury and Preserves Rapid patial Learning in a Model of Traumatic Brain Injury", J Neuropathol Exp Neurol, Dec. 2010, pp. 1177-1190, vol. 69, No. 12, Maryland.

Pompermayer et al, "Effects of the Treatment with Glibenclamide, an ATP-Sensitive Potassium Channel Blocker, on Intestinal Ischemia and Reperfusion Injury", European Journal of Pharmacology, 2007, pp. 215-222, vol. 556, Brazil.

Pompermayer et al, "The ATP-Sensitive Potassium Channel Blocker Glibenclamide Prevents Renal Ischemia/Reperfusion Injury in Rats", Kidney International,2005, pp. 1785-1796, vol. 67, Brazil.

Porikos et al, "Diet induced changes in serum transaminase and triglycreride levels in healthy adult men", Am J Med, 75:624-30, 1983.

Purkins et al, "The influence of diet upon liver function tests and serum lipids in healthy male volunteers resident in a Phase 1 unit", British Journal of Clinical Pharmacology 57:2, 199-208, 2003.

Rogers et al, "Pharmacokinetics of intravenous glibenclamide investigated by a high performance liquid chromatographic assay", Diabet, 1982, 23:37-40.

Rydberg et al, "Comparison of the kinetics of glyburide and its active metabolites in humans", J. Clin. Pharm. Ther, 1995, 20(5):283-295.

Rydberg et al, "Hypoglycemic activity of glyburide (glibenclamide) metabolites in humans", Diabet. Care, 1994, 17:1026-103.

Sayuk et al, "Hepatic glycogenosis: An under-recognized source for abnormal liver function tests", Dig Dis Sci., 52:936-938, 2007.

Simard et al, "Endothelial Sulfonylurea Receptor 1-Regulated NCCa-ATP Channels Mediate Progressive Hemorrhagic Necrosis Following Spinal Cord Injury", Journal of Clinical Investigation, May 2007, pp. 9, Baltimore, MD.

Simard et al, "Glibenclamide is Superior to Decompressive Craniectomy in a Rat Model ofMilignant Stroke *Online-Only Data Supplement (Methods)", Stroke: Journal of the AHA, 2010, pp. 10, ISSN: 1524-4628, Dallas, TX.

Simard et al, "Key Role of Sulfonylurea Receptor 1 in Progressive Secondary Hemorrhage Following Brain Contusion", Journal ofNeurotrauma, 2009, pp. 42, New Rochelle, NY.

Simard et al, "Newly Expressed SURI-Regulated NCCa-ATP Channel Mediates Cerebral Edema After Ischemic Stroke", Nature Medicine, Apr. 2006, pp. 433-440, vol. 12, No. 4, Baltimore MD.

Simard et al, "Protective Effect of Delayed Treatment with Low-Dose Glibenclamide in Three Models ofIschemic Stroke *Supplemental Methods", Stroke: Journal of the AHA, 2009, pp. 8, ISSN: 1524-4628, Dallas, TX.

D'Arcy, PF (ED): "Drug interactions with medical plastics", Drug Intelligence and Clinical Phar, Cincinnati, OH, US, vol. 17, No. 10, 1983, pp. 726-731.

(56) References Cited

OTHER PUBLICATIONS

Fukazawa, T., et al: Reduction of non-specific adsorption of drugs to plastic containers used in bioassays or analyses 11, Journal of Pharmacological and Toxicological Methods.,vol. 61, No. 3, 2010,pp. 329-333.

De Muynck, C., et al: "Binding of Drugs to End-Line Filters: A Study of Four Commonly Administered Drugs in Intensive Care Units", Journal of Clinical Pharmacy and Therapeutics.,vol. 13, No. 5., 1988, pp. 335-340.

Weltje, L., et al: "Adsorption of metals to membrane filters in view of their speciation in nutrient solution", Environmental Toxicology and Chemistry., vol. 22. No. 2., 2003, pp. 265-271.

Breme, F., et al: Coating of polymers with titanium-based layers by a novel plasma-assisted chemical vapor deposition process 11, Thin Solid F, Elsevier, Amsterdam, NL, vol. 377-378, 2000, pp. 755-759.

Anonymous: 11 Alternatives to PVC for IV bags : Packaging Digest 11, 2002, XP055468910, Retrieved from the Internet: URL:http://www.packagingdigest.com/drug-delivery/pmp-alternatives-pvc-iv-bags-020417.

Panten, U., et al: 11 Control of insulin secretion by sulfonylureas, meglitinide and diazoxide in relation to their binding to the sulfonylurea receptor in pancreatic islets. Biochemical Pharmacology. Elsevier. US, vol. 38. No. 8, 1989, pp. 1217-1229.

Extended European Search Report dated May 18, 2018 cited in European Application No. 18157269.4, 11 pages.

Translation of Notice of Reasons for Rejection dated Jun. 11, 2018 in JP2017-51153, 7 pages.

Sorgel et al, "New Investigation of glibenclamide's bioavailability", Pharm. Res, 1997, 14:S251.

Spraul et al, "Uniform elimination pattern for glibenclamide in healthy Caucasian males", Arzneimittelforschung, 1989, 39(11):1449-1450.

Grover et al., The J. of Pharmacology and Experimental Therapeutics, 297 (3), pp. 1184-1192.

Chen et al. "Impact of Infusion Apparatus on Clinical Medication Safety", China Pharmacy, 2007, vol. 18, No. 26, pp. 2073-2075 (Partial Translation).

Notice of Preliminary Rejection cited in Korean Application No. 10-2018-7032015 dated Aug. 26, 2019, with an English translation, 12 pages.

Notice of Reasons for Rejection cited in Japanese Patent Application No. 2018-230763 dated Sep. 20, 2019 with a English translation, 16 pages.

Lee, "Sorption of four drugs to polyvinyl chloride and polybutadiene intravenous administration sets", American Journal of Hospital Pharmacy, vol. 43, Aug. 1986, pp. 1945-1950.

Pearson, J.G., "Pharmacokinetics of Glyburide", The American Journal of Medicine, vol. 79, (suppl 3B), Sep. 1985, pp. 67-71.

Mean plasma glyburide concentrations for 6 mg/day RP-1127 dose

Mean plasma glyburide concentrations for 10 mg/day RP-1127 dose

Median Blood Glucose Levels for placebo, 0.4 mg/day and 3 mg/day

METHODS OF INTRAVENOUS ADMINISTRATION OF GLYBURIDE

CROSS-REFERENCE TO RELATED APPLICATIONS

This application is a continuation of and claims priority to U.S. patent application Ser. No. 15/686,989 filed Aug. 25, 2017, which is a continuation of and claims priority to U.S. patent application Ser. No. 15/425,874, filed Feb. 6, 2017, now U.S. Pat. No. 10,052,280, which is a continuation of and claims priority to U.S. patent application Ser. No. 15/422,358, filed Feb. 1, 2017; which is continuation of and claims priority to U.S. patent application Ser. No. 14/878,232, filed Oct. 8, 2015, now U.S. Pat. No. 9,561,176; which is a continuation of and claims priority to U.S. patent application Ser. No. 14/525,992, filed on Oct. 28, 2014, now U.S. Pat. No. 9,254,259; which is a continuation of and claims priority U.S. patent application Ser. No. 13/811,037, filed on Mar. 21, 2013, now U.S. Pat. No. 8,946,293, which was a National Stage Application under 35 U.S.C. § 371 of International Application No. PCT/US2011/044397, filed Jul. 18, 2011, which claimed priority under 35 U.S.C. § 119(e) and the benefit of U.S. Provisional Application Ser. No. 61/365,689, filed Jul. 19, 2010, the entire disclosures of which are hereby incorporated by reference in their entireties.

FIELD OF THE INVENTION

This invention relates to the field of medical treatment methods, including intravenous methods of administration of drugs to a subject.

BACKGROUND

Glyburide (also known as, e.g., glibenclamide) is a sulfonylurea drug used in treating diabetes. The systematic name of glyburide is 5-chloro-N-(4-[N-(cyclohexylcarbamoyl) sulfamoyl]phenethyl)-2-methoxybenzamide. Glyburide preferentially binds to and affects the sulfonylurea receptor 1 (SUR1) but at higher concentrations also binds to and affects the sulfonylurea receptor 2 (SUR2).

Glyburide has been suggested as a therapy for acute stroke (ischemic and hemorrhagic), traumatic brain injury (TBI), spinal cord injury (SCI), myocardial infarction (MI), shock (including hemorrhagic shock), organ ischemia, and ventricular arrhythmias. The pharmacokinetic parameters of intravenous glyburide have been described in numerous publications (see Table 1). All patents and publications discussed herein are hereby incorporated by reference in their entireties.

TABLE 1

Pharmacokinetic Parameters of Glyburide after Intravenous Administration

| | McEwen[1] | Spraul[2] | Rydberg[3] | Rogers[4] | Sorgel[5] | Morrison[6] | Neugebauer[7] | Jonsson[8]† |
|---|---|---|---|---|---|---|---|---|
| | | | | Patient Population | | | | |
| | Healthy males | Healthy males and females | Healthy males and females | Healthy males and females | Healthy males | Healthy males and females | NIDDM(Non insulin dependent diabetes mellitus) males and females | Healthy males and females |
| N | 20 | 52 | 8 | 8 | 24 | 8 | 20 | 10 |
| Dose (mg) | 1.48‡ | 4.0 | 1.0 | 1 | 1.5 | 2.4 | 1.25 | 2.0 |
| $C_{max}$ (ng/mL) | — | — | — | — | 331 ± 65 | 648 | 376 | 196 |
| Clearance: (L/h) | 2.92‡ | — | 5.46*‡ | — | — | 4.42 | 4.41 | 1.68‡ |
| (mL/min) | 49 | — | 91*‡ | — | 74.7 ± 22 | 73.7‡ | 73.5‡ | 101.3 |
| $V_d$ (L) | 9.7‡ | — | 10.9*‡ | — | 11.22 ± 3 | 7.4 | 11.6‡ | — |
| Beta (1/h) | 0.3 | — | 0.52*‡ | 0.517 | — | 0.62 | 0.38 | — |
| $t_{1/2}$ (h) | 2.46 | 1.50 ± 0.36 | 1.47 ± 0.42 | 1.47 | 4.22 ± 1 | 1.18‡ | 1.82 | 1.15 |
| Tmax(h) | — | — | — | — | 0.09 | — | — | — |
| Mean subject weight (kg) | 74.1 | — | 74.6 | 57-88 | — | 69.7 | — | — |

*normalized to 70 kg
†Data from Caucasian patients
‡Not presented in the publication, data generated from information presented in the publication.
AUC, area under the time-concentration curve; $C_{max}$, the maximum concentration of the drug; $V_d$, the volume of distribution of drug
[1]McEwen, et al. 1982;
[2]Spraul et al. 1989;
[3]Rydberg et al. 1995;
[4]Rogers et al. 1982;
[5]Sorgel et al. 1997;
[6]Morrison et al. 1982;
[7]Neugebauer et al. 1985;
[8]Jonsson et al. 2000.

While the intravenous ("i.v." or "IV") glyburide dose in these and other studies was delivered within a few minutes in the majority of studies, several of the studies included continuous infusions of an hour or more. Garrel et al. (1987) administered a 1 mg i.v. bolus dose, followed by 0.3 mg/h for 17 hours, to six subjects with IDDM (insulin-dependent diabetes mellitus); the total dose was 6.1 mg glyburide. In addition, Groop et al. (1987) dosed 16 normal subjects with a total of 2.1 mg over 4 hours, and Neugebauer et al. (1985) dosed ten normal subjects with a total of 2 mg i.v. glyburide over 1 hour.

Doses for bolus infusions (i.e., infusions of three minutes or less) ranged between 1 and 2.4 mg (Rydberg et al. 1994).

The doses and duration of dosing of the studies described above are presented in Table 2.

TABLE 2

Dose and Duration of Dosing in Select Clinical Studies of Intravenous Glyburide.

| | Garrel et al. 1987 | Groop et al. 1987 | Neugebauer et al. 1985 | Rydberg et al. 1994 | Bank et al. 2000 |
|---|---|---|---|---|---|
| N | 6 | 16 | 10 | 8 | 12 |
| Bolus dose | 1 mg | 0.84 mg | N/A | 2.4 mg | — |
| Duration of infusion | 17 hours | 4 hours | 1 hour | — | 10 min |
| Infusion dose/hr | 0.3 mg/hr | 0.35 mg/hr | 2 mg/hr | — | 6 mg/hr |
| Bolus dose | 1 mg | 0.84 mg | N/A | 2.4 mg | — |
| Total dose | 6.1 mg | 2.1 mg | 2 mg | 2.4 mg | 1 mg |

Maximum glyburide plasma concentrations were provided for some studies, and ranged from 200-436 ng/mL (Rogers et al. 1982; Groop et al. 1987; Bank et al. 2000; Jonsson et al. 2000). Subjects in the study by Groop et al. (1987), who received a bolus dose followed by continuous i.v. infusion, reached a mean glyburide $C_{max}$ of 240 ng/mL after administration of the bolus, and a steady-state concentration of 88-93 ng/mL during the 220 minutes of continuous infusion.

SUMMARY OF THE INVENTION

Methods of administering glyburide, or other drug, are disclosed. The novel methods disclosed herein include methods of administering glyburide, or other drug, over periods of more than an hour to a subject, and preferably over periods of many hours (e.g., about 72 hours or about 96 hours or about 120 hours), and in particular include intravenous methods of administering glyburide, or other drug, to a subject. The methods disclosed herein may be useful for treating a subject in need of treatment for, e.g., acute stroke (ischemic and hemorrhagic), traumatic brain injury (TBI), spinal cord injury (SCI), myocardial infarction (MI), shock (including hemorrhagic shock), organ ischemia, and ventricular arrhythmias. In these and other indications, the use of intravenous glyburide is preferable as targeted glyburide plasma levels can be more quickly and reliably be reached and maintained. The methods disclosed herein provide rapid achievement of therapeutic levels of glyburide, or other drug, following initiation of drug administration, and also provide for maintenance of therapeutic levels of glyburide, or other drug, over an extended period of time, (e.g., for about 72 hours or about 96 hours or about 120 hours). In addition, the methods disclosed herein provide rapid achievement of therapeutic drug levels, maintenance of therapeutic drug levels for an extended period of time, and further avoid excessive levels of drug and so avoid possible drug side-effects.

Embodiments of the methods of administering glyburide, or other drug, to a subject include intravenous administration of a bolus of glyburide, or other drug, followed (either substantially immediately, or after a delay after completion of the bolus administration) by a continuous infusion of glyburide, or other drug. Further embodiments of the methods of administering glyburide, or other drug, to a subject include intravenous administration of a first bolus of glyburide, or other drug, followed (either substantially immediately, or after a delay after completion of the bolus administration) by a continuous infusion of glyburide, or other drug, followed by a second bolus of glyburide, or other drug. In further embodiments, a second infusion may follow a second bolus. In yet further embodiments, multiple boluses and multiple infusions may be administered to a subject.

In embodiments, the administration of glyburide to a subject extends over periods of more than an hour to a subject; in particular embodiments, the methods of administration of glyburide to a subject are intravenous methods of administration of glyburide to a subject where the administration extends over periods of more than an hour. For example, in embodiments, administration of glyburide, or other drug, extends over periods of more than about 72 hours. In other embodiments, administration of glyburide, or other drug, extends over periods of more than about 10 hours, or more than about 20 hours, or more than about 30 hours, or more than about 40 hours, or more than about 50 hours, or more than about 60 hours, or more than about 70 hours.

The methods of administration include administration of glyburide in a bolus injection to a subject, where the bolus injection is administered to the patient over a period of time of about 3 minutes or less; and where the bolus administration is followed by a continuous infusion of glyburide. In embodiments, the bolus is followed substantially immediately by the initiation of the continuous infusion (e.g., the continuous infusion commences less than one hour, or less than 30 minutes, or less than 10 minutes, or less than 5 minutes, or less than 3 minutes, or less than 2 minutes, or less than 1 minute, after the completion of the bolus administration).

In further embodiments, the methods of administration include administration of glyburide in a bolus injection to a subject, where the bolus injection is administered to the patient over a period of time of about 3 minutes or less; and where the bolus administration is followed by a continuous infusion of glyburide, or other drug, and by one or more further bolus injections of glyburide, or other drug. In embodiments, a second bolus injection is administered substantially immediately after the completion of the continuous infusion (e.g., the second bolus administration commences less than one hour, or less than 30 minutes, or less than 10 minutes, or less than 5 minutes, or less than 3 minutes, or less than 2 minutes, or less than 1 minute, after the completion of the continuous infusion). A second continuous infusion may begin substantially immediately after the completion of the second bolus injection, or a second continuous' infusion may begin after an extended period of time after the completion of the first continuous infusion. In embodiments, a third bolus injection may begin after the completion of the second continuous infusion, and may begin either substantially immediately after the completion of the second continuous infusion, or may begin after an extended period of time after the completion of the second continuous infusion. Similarly, a fourth, or fifth, or other further bolus injection, and/or further continuous infusion may be administered, either substantially immediately, or after an extended period of time.

In further embodiments, multiple bolus injections of glyburide, or other drug, may be administered to a subject, without an intervening continuous infusion of glyburide, or other drug. In addition, in yet further embodiments, multiple continuous infusions of glyburide, or other drug, may be administered to a subject, without an intervening bolus injection of glyburide, or other drug. Such multiple bolus injections, or continuous infusions, or combinations thereof, may be administered substantially immediately after the previous injection or infusion, or may be administered after an extended period of time after the previous injection or infusion. A continuous infusion provides the administration of glyburide, or other drug, over an extended period of time, where an extended period of time may be a period of time measured in minutes (e.g., a few or several or many minutes), or measured in hours (e.g., a few or several or many hours), or measured in days (e.g., a few or several or many days).

In embodiments of the methods disclosed herein, the concentration of glyburide, or other drug, is higher in the formulation administered by bolus injection than the concentration of glyburide, or other drug, in the formulation administered by continuous infusion.

Applicant discloses herein that the blood levels of glyburide in human subjects typically reaches a peak level some hours following initiation of glyburide administration (e.g., after initiation of a bolus injection of glyburide followed by a continuous infusion of glyburide to the subject).

In a particular embodiment, Applicant discloses herein a 3 phase dosing regimen suitable for overcoming the dip in glyburide plasma levels which occurs several hours following the initiation of glyburide administration. In embodiments, such a 3 phase dosing regimen comprises:

(a) a bolus followed by a second bolus followed by a continuous infusion (b) a bolus followed by an infusion at Rate 1 for A Hours followed by an infusion at Rate 2 for the remainder of the dosing period, where Rate 1>Rate 2 and A ranges from 1-20 hours. ("Rate 1" refers to a first rate, and "Rate 2" refers to a second rate, of administration of glyburide, or other drug, typically measured as, e.g., micrograms per hour (μg/hr).)

In a further embodiment, administration of glyburide, or other drug; is provided by 4 or more phases in the dosing regimen where multiple boluses and/or multiple infusion rates can be used. In such an embodiment, multiple rates and durations of administration are also provided (e.g., a Rate 1, Rate 2, Rate 3, Rate 4, etc.; and time periods A, B, C, etc.).

For example, Rate 1 may vary between about 15 μg/hr and about 200 to 300 μg/hr (e.g., between about 16.7 μg/hr and 250 μg/hr), and Rate 2 may vary between about 15 μg/hr and about 200 to 300 μg/hr (e.g., between 16.7 and 250 μg/hr). For example, time period A may vary from about 1 to about 10 hours, or from about 1 to about 20 hours. The total amount of glyburide, or other drug, delivered to the subject is the sum of the amount delivered by the bolus injection(s) plus the amount delivered during the continuous infusion. The amount of glyburide, or other drug, delivered to the subject during continuous infusion is calculated by multiplying the Rate times the time period (e.g., Rate 1× time period A). In embodiments, the daily dose (the dose over a 24 hour period, for example, the dose for the first 24 hours of glyburide administration) may be determined as follows: first Bolus+Rate 1×A+Rate 2×(24-A). In embodiments, the dose for the first 24 hours will be less than about 6 mg, or less than about 5 mg, or less than about 4 mg, and preferably may be less than about 3.5-4 mg, or less than about 3.13 mg or less than about 3 mg.

Thus, in embodiments, it is preferred that the total amount of glyburide administered to the subject per day be less than about 10 mg, or more preferably less than about 8 mg, or more preferably less than about 6 mg, and still more preferably less than about 5 mg, or yet still more preferably less than about 4 mg, or even more preferably less than about 3 mg of glyburide per day.

In a further embodiment, a bolus of about 125-150 μg, e.g., about 130 μg, of glyburide is administered to a subject followed by a continuous infusion of about 150-175 μg/hr, e.g., about 163 μg/hr, of glyburide for about 6 hours and then a further continuous infusion of about 100-125 μg/hr, e.g. about 112 μg/hr, glyburide is administered for about 50-75 hours, e.g. about 66 hours, for a total dosing period of about 72 hours. Thus, in this embodiment, the total daily dose of glyburide on Day 1, Day 2 and Day 3 may be about 3-4 mg, 2.5-3 mg, and 2.5-3 mg; e.g., about 3 mg, 2.5 mg, and 2.5 mg, respectively; or about 3.12 mg, 2.69 mg, and 2.69 mg respectively.

In a yet further embodiment, a bolus of glyburide, or other drug, is administered, and the bolus is followed by a continuous infusion of glyburide, or other drug, and then a further bolus or further boluses is/are administered, effective to raise early plasma levels of glyburide, or other drug, to desired levels. For instance, such an embodiment of the methods disclosed herein would include administration of a bolus of 125-150 μs, e.g., about 130 μg, glyburide followed by a continuous infusion of 100-125 μg/hr, e.g., about 112 μg/hr of glyburide, with a second glyburide bolus of 125-150 μs, e.g., about 130 μg, administered at hour 1, 2, or 3. In embodiments, further boluses may be administered as well.

In a further embodiment, Applicant discloses herein a method of administering glyburide, or other drug, to a subject, comprising: (a) a bolus administration of glyburide, or other drug; (b) a first continuous infusion administration of glyburide, or other drug after said bolus administration of glyburide, or other drug, wherein in said first continuous infusion glyburide, or other drug, is administered at a first rate of administration for a first period of time; and (c) a second continuous infusion administration of glyburide, or other drug after said first continuous infusion of glyburide, or other drug, wherein in said second continuous infusion glyburide, or other drug, is administered at a second rate of administration for a second period of time; whereby glyburide, or other drug, is administered to a subject effective to provide a substantially steady level of glyburide, or other drug, in the blood of said subject over a desired period of time. In a particular example of this further embodiment, the bolus is a bolus of about 125-150 μg, e.g., about 130 μg, of glyburide, and the bolus is followed by a continuous infusion of about 150-175 μg/hr, e.g., about 163 μg/hr of glyburide for about 6 hours; and then a further continuous infusion of about 100-125 μg/hr, e.g., about 112 μg/hr glyburide is administered to the subject for about 66 hours, for a total period of glyburide administration of about 72 hours. The total daily dose of glyburide on Day 1, Day 2 and Day 3 is thus about 3 mg, 2.5 mg, and 2.5 mg respectively; or about 3.12 mg, 2.69 mg, and 2.69 mg respectively.

Dosing of glyburide, or other drug, may be determined as a function of a subject's weight, or age, or gender, or height, or body surface area, or a combination of one or more of these, and the rates and bolus may be expressed as a function of one or more of these measures or methods of dosing.

The methods disclosed herein provide advantages for treating subjects in need of a fairly steady amount of glyburide introduced rapidly and maintained over an extended period of time (e.g., for up to about 72 hours). For example, where a subject has suffered a stroke, or traumatic brain or spinal cord injury, rapid achievement of therapeutic levels of glyburide may be important to a successful therapeutic outcome; in addition, maintenance of such therapeutic levels may likewise be important to a successful therapeutic outcome; however, it may also be important to prevent sustained levels of glyburide that are too high for the subject (e.g., to avoid hypoglycemia, extensive action of glyburide on the SUR2 receptor, or other complications). The experimental results and methods disclosed herein provide methods for achieving and maintaining therapeutic levels of glyburide rapidly, and over an extended period of time, and provide methods for avoiding excessive levels of glyburide, and so provide useful and advantageous treatments for subject in need of glyburide treatment. Subject in need of such treatments may include, for example, subjects suffering from acute stroke (ischemic and hemorrhagic), traumatic brain injury (TBI), spinal cord injury (SCI), myocardial infarction (MI), shock (including hemorrhagic shock), organ ischemia, and ventricular arrhythmias.

It will be understood that other drugs, in addition to glyburide, may be administered to a subject according to the methods disclosed herein. Administration of such other drugs may be particularly advantageous where the other drug has a pharmacokinetic profile similar to that of glyburide, as disclosed herein, or shares some of the pharmacokinetic properties of glyburide.

Applicants have discovered that it is preferable to avoid contact of a glyburide solution with polyvinyl chloride (PVC), as Applicants have discovered that the concentration of glyburide is reduced in glyburide solutions placed in contact with PVC. Applicants have invented methods to minimize such reductions of the concentration of glyburide in glyburide solutions placed in contact with PVC, and have invented methods of administration of glyburide which avoids contact of glyburide solutions with PVC. For example, Applicants have discovered that use of polyethylene bags, tubing, and filters, or polyethylene-coated bags and tubing, is preferred for the administration of glyburide solutions over the use of PVC-containing bags, tubing and filters.

Applicants disclose herein methods of preparing a container or device used in the administration of glyburide, e.g., in the administration of a therapeutic glyburide solution to a patient in need of such a therapeutic solution, are provided herein. Such methods of preparing a container or device, such as preparing a container, tube, and/or filter, comprise contacting a container, a tube, or a filter with a glyburide flushing solution. Such methods may include, for example, flushing a container, tube and/or filter with said glyburide flushing solution prior to its use in the administration of glyburide; the flushing may include flushing with at least about 50 mL, or at least about 70 mL, or more of the glyburide flushing solution. A glyburide flushing solution may have a glyburide concentration of at least about 2 µg/mL of glyburide, or about 2 µg/mL to about 8 µg/mL of glyburide, or about 5 to 6 µg/mL of glyburide, or greater concentrations of glyburide. Such methods include use of containers and devices, including bags, tubes, and filters which may have polyvinyl chloride (PVC) surfaces that may contact said glyburide therapeutic solution.

Applicants disclose herein methods of administering a glyburide therapeutic solution, wherein a container, a tube, and/or a filter is contacted (e.g., flushed) with a glyburide flushing solution prior to use of the container, tube, or filter in the administration of said glyburide therapeutic solution. The flushing may be flushing with at least 50 mL, or about 70 mL, or more, of the glyburide flushing solution. The glyburide flushing solution may have a glyburide concentration of at least about 2 µg/mL, or about 2 to about 8 µg/mL, or more of glyburide. The surfaces of containers, tubes, and/or a filters used for the administration of a glyburide therapeutic solution are preferably made of one or more materials other than polyvinyl chloride (PVC), for example, with polyethylene, in order to avoid contact of the glyburide therapeutic solution with PVC.

Applicants further provide methods of administering glyburide therapeutic solutions, in which a high concentration glyburide solution (e.g., at least about 10 µg/mL glyburide) is filtered and then diluted to provide a glyburide therapeutic solution (typically of lower glyburide concentration than the high concentration glyburide solution), and administering the glyburide therapeutic solution using delivery means made of one or more materials other than polyvinyl chloride (PVC), such as, e.g., polyethylene. A high concentration glyburide solution may have a glyburide concentration of between about 0.5 mg/mL glyburide and about 1 mg/mL glyburide, and may have a glyburide concentration of at least about 1 mg/mL glyburide. The glyburide therapeutic solution may be stored after filtering and prior to administration; in embodiments, the filtered glyburide therapeutic solution is stored within a container having an inner surface in contact with said glyburide therapeutic solution, wherein said container inner surface is made from one or more materials other than polyvinyl chloride (PVC), such as, e.g., polyethylene.

Applicants further provide methods of treating a patient in need of treatment, comprising identifying a patient in need of treatment for stroke, traumatic brain injury, spinal cord injury, myocardial infarction, shock, organ ischemia, ventricular arrhythmias, ischemic injury, or hypoxia/ischemia; administering a bolus of glyburide to the patient; and administering a continuous infusion of glyburide to the patient at from about 15 µg/hr and about 300 µg/hr, wherein the continuous infusion glyburide is administered for a period of time more than about 20 hours.

It will be understood that solutions discussed herein, such as glyburide solutions, and including without limitation, glyburide therapeutic solutions, glyburide flushing solutions, high concentration glyburide solutions, and other solutions may be filtered, and that such filtering is preferably sterile filtering, effective to provide sterile solutions suitable for administration to a patient. Such sterile filtration may include, for example, filtration through a sterile 0.2 micron filter, or other sterile filter suitable for use in providing sterile filtered solutions.

DETAILED DESCRIPTION OF THE INVENTION

Definitions

Figure 1:
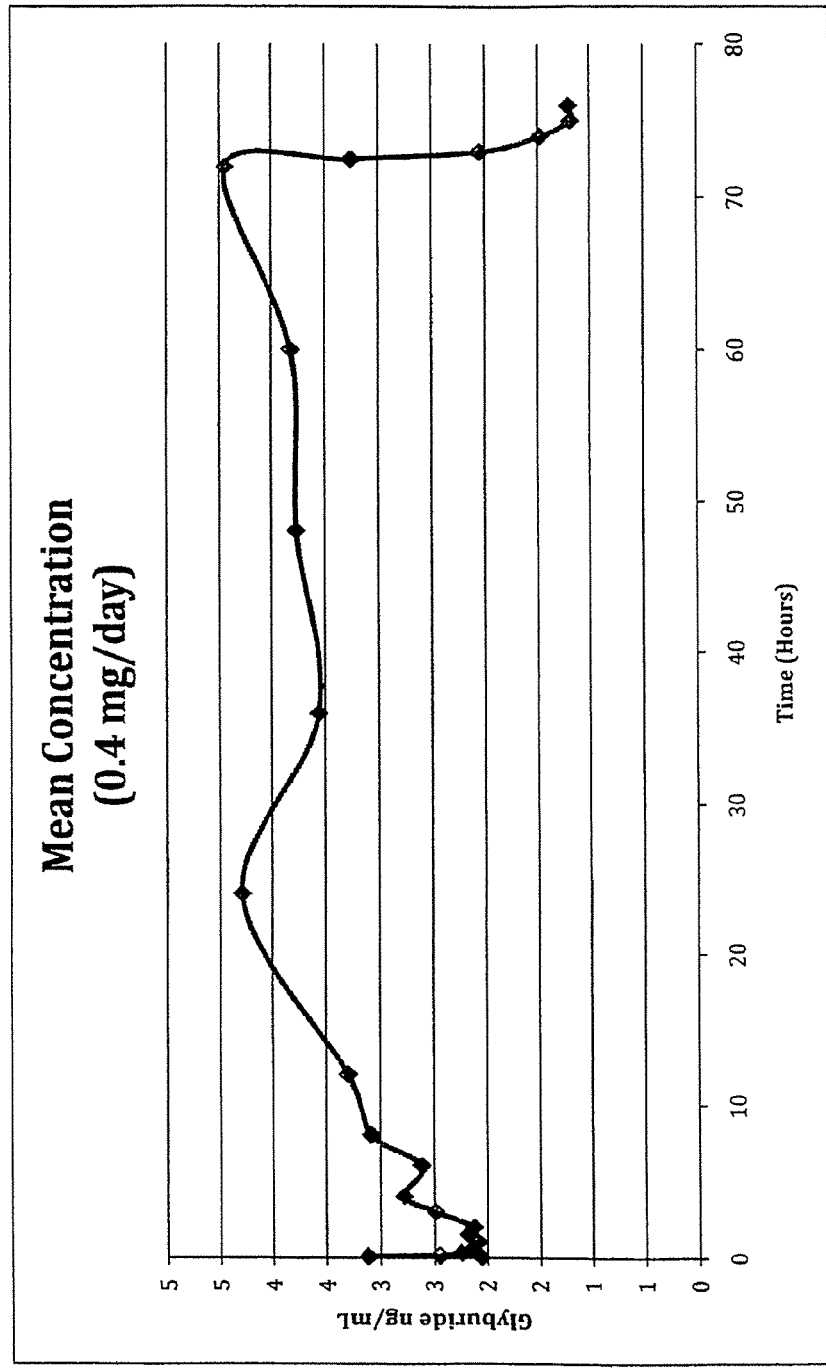
FIG. 1—Mean plasma glyburide concentrations for 0.4 mg/day glyburide.

Terms used herein would be understood by those of skill in the art, and are to be understood in the manner accepted by those of skill in the art. Further definitions are provided herein to further explain and define terms.

As used herein, "patient," "volunteer," "subject" and the like, whether singular or plural, refers to human patients, volunteers, subjects, and the like.

As used herein, "ALT" is an acronym and means alanine transaminase.

As used herein, "AST" is an acronym and means aspartate transaminase.

As used herein, the term "dose" and its grammatical equivalents refer to the amount of glyburide administered to a subject. A dose may be described in terms of the grams of glyburide, or in terms of the weight/volume of diluent administered to the subject (e.g., milligrams per milliliter: mg/mL; micrograms per milliliter: µg/mL; nanograms per milliliter: ng/mL; etc.). The glyburide may be in water, such as sterile water for injection or other suitable water; in saline; in sugar solution; or in any pharmaceutically acceptable solution, which may include any other pharmaceutically acceptable drugs, excipients, osmoticants, diluents, buffers, preservatives, or other compounds or additives suitable for use in a fluid for injection.

As used here, the term "$C_{max}$" indicates the maximum concentration, in the blood, of glyburide.

As used here, the term "AUC" indicates area under the curve (the integral of the plasma concentration of the drug over an interval of time), and is used as a measure of the total amount of glyburide, or other drug, to which the subject is exposed by the drug administration.

As used here, the term "clearance" refers to the loss of glyburide, or other drug, from the blood of the patient. Clearance refers to a fraction of a (theoretical) volume of plasma from which the drug has been completely removed, per unit of time. Clearance may be measured, for example, in liters per hour (L/h), in milliters per minute (mL/min).

As used herein, the term "$V_d$" refers to volume of distribution, a term known to those of skill in the art, which refers to the volume (or potential volume) into which a drug, such as glyburide, would be distributed in a subject's body if it were distributed homogeneously (i.e., at the same concentration throughout that volume). Volume of distribution is typically measured in liters or liters per kilogram (L or L/kg).

As used herein, the term "Beta" provides a measure of the rate of transport of a drug, such as glyburide, into or out of the blood and tissue of a subject.

As used herein, the term "$t_0$" or "$t_{zero}$" refers to the initial time, from which further time measurements are taken. For example, where glyburide or other drug is administered to a subject, the time $t_0$ is the time at which administration commences. This initial time, the time $t_0$, is the time at which administration commences whether the administration is bolus administration, continuous infusion, bolus administration followed by continuous infusion, administration with periods of time in which no drug, or different amounts of drug, are administered, or combinations of these.

As used herein, the term "$t_{1/2}$" refers to the half-life, typically measured in hours (h), minutes (min) or seconds (s), of a drug that has been administered to a subject. For example, the time to which the level (e.g., concentration) of glyburide or other drug (in the blood of a subject to which glyburide or other drug has been administered) drops to half its previous value is the $t_{1/2}$ for that subject.

As used herein, the term "$t_{max}$" refers to the time to which the level (typically concentration in the blood) of a drug that has been administered to a subject reaches its maximum level. For example, the time to which the level (e.g., concentration) of glyburide or other drug (in the blood of a subject to which glyburide or other drug has been administered) reaches its maximum after initial administration is the $t_{max}$ for that subject.

As used herein, the term "bolus" refers to administration of glyburide or other drug in a single injection that lasts for a relatively short period of time. As used herein, a bolus lasts for a period of time of about 3 minutes or less. A bolus injection may be an injection of a relatively high dose or concentration of drug.

As used herein, the term "continuous" refers to administration of glyburide or other drug in an injection that lasts for an extended period of time. A continuous injection may be an injection of a moderate dose or concentration of drug, or of a relatively low dose or concentration of drug. The term "infusion" is often used with continuous injection; as used herein, "continuous injection" and "continuous infusion" both equally refer to the intravenous administration of a drug, such as glyburide, to a patient over an extended period of time.

As used herein, an "extended period of time" refers to a period of time that is longer than one or two or three minutes. For example, an extended period of time may be a period of about 10 minutes, or about 20 minutes, or about 30 minutes, or about 40 minutes, or about 50 minutes, or more. In further examples, an extended period of time may be a period of about one hour, or about 2 hours, or about 3 hours, or about 4 hours, or about 5 hours, or about 6 hours, or about 7 hours, or about 8 hours, or about 9 hours, or more. In further examples, an extended period of time may be a period of about 10 hours, or about 12 hours, or about 15 hours, or about 20 hours, or about 25 hours, or about 30 hours, or about 40 hours, or about 44 hours, or about 48 hours, or more. It will be understood that an extended period of time may also be a period of about one day, or about two days, or about three days, or about four days, or about five days, or more.

As used herein, "substantially immediately" refers to a period of time that is less than about one hour, or less than 30 minutes, or less than 10 minutes, or less than 5 minutes, or less than 3 minutes, or less than 2 minutes, or less than 1 minute, after a previous event or time period.

As used herein, the term "placebo" refers to an ostensibly pharmaceutical formulation which lacks a pharmaceutically active ingredient, or lacks the particular pharmaceutical ingredient of interest in a particular study. In the experiments disclosed herein, "placebo" refers to a formulation identical to the formulation given to test subjects but lacking glyburide (e.g., including mannitol and NaOH, but not including glyburide). In general, a placebo may include inert compounds, and any pharmaceutically acceptable compound which may be found in a medicament, so long as it lacks a pharmaceutically active ingredient (as determined with respect to the pharmaceutical ingredient to which it is to be compared).

As used herein, the term "BG" refers to blood glucose.

As used herein, the term "PRN" means prescribed as needed.

In the following, time periods may be indicated as hours (e.g., HI0 indicates at hour 10, or 10 hours following initiation of treatment) or days (e.g., D2 indicates day 2, or the second day following initiation of treatment).

The term "DSW" as used herein indicates water with 5 grams (g) of dextrose per 100 milliliters (mL) of water.

"RP-1127" refers to glyburide, or to glyburide formulations.

Applicant has performed experiments including the administration of glyburide and of placebo to subjects. Results of these experiments are disclosed in the following examples.

Examples

Glyburide Storage and Administration
Phase 1 Study

We determined through in-use stability testing that glyburide concentration is reduced by contact with polyvinyl chloride (PVC). For example, glyburide concentration is reduced when a glyburide-containing solution is passed through PVC tubing, or stored in a PVC bag. For example, we determined that glyburide concentration is reduced when glyburide-containing solutions are stored in PVC bags at glyburide concentrations below 10 µg/mL. One possible explanation is that glyburide adsorbs to PVC. At 10 µg/mL glyburide we were able to use a standard PVC bag (but not PVC tubing) with an acceptable amount of loss of glyburide (e.g., loss presumably due to adsorption to PVC).

We further discovered that glyburide concentration in a glyburide-containing solution is reduced by passage though a filter, such as through a 0.2 micron in-line filter. Thus in the human experiments in the application, e.g., for continuous infusion, glyburide was administered through low sorbing polyethylene (PE)-lined tubing with an inline filter that had been flushed according to a predetermined flushing protocol (see below) designed to ensure that the concentration of glyburide was reduced by no more than about 10%. For the lower doses, i.e. 0.4 mg/day, 3 mg/day and 6 mg/day (in which the glyburide concentration was less than 10 µg/mL), we used PVC-free bags. For the 10 mg/day dose (in which the glyburide concentration was 10 µg/mL), we used PVC bags.

For bolus injections, at all concentrations, we used a PALL Pharmassure 0.2 micron filter, HP1002 (Pall Life Sciences, 600 South Wagner Road, Ann Arbor, Mich. 48103) that had been flushed with the glyburide solution to be administered (ranging from about 2-3 µg/mL to about 50-75 µg/mL, e.g., ranging from about 2.5 µg/mL to about 60 µg/mL (for example, from 2.48 µg/mL to about 62.00 µg/mL) prior to use for injection.

Specifically:
- The PVC free bag used was the B Braun EXCEL L8000 (B. Braun Medical Inc., 824 Twelfth Avenue, Bethlehem, Pa. 18018.
- The PVC bag used was the Viaflex 1,000 mL 2B1324X (Baxter, One Baxter Parkway, Deerfield, Ill. 60015-4625).
- The Carefusion 2260-0500 (CareFusion Corporation, 3750 Torrey View Court, San Diego, Calif. 92130) low sorbing administration set attached to an Carefusion 20350E (CareFusion Corporation, 3750 Torrey View Court, San Diego, Calif. 92130) low sorbing extension set with a 0.2 micron low protein binding filter was used for administering glyburide at 10 µg/mL concentration.
- The Carefusion 10010454 (CareFusion Corporation, 3750 Torrey View Court, San Diego, Calif. 92130) low sorbing administration set with built in 0.2 micron filter was used for administration of glyburide at concentrations below about 10 µg/mL.
- An Alaris Pump unit (CareFusion Corporation, 3750 Torrey View Court, San Diego, Calif. 92130) compatible with the above products was used.

TABLE 1

Flushing Protocols for Infusion and Bolus Administration

| Concentration (µg/mL) | Equipment Used | Flushing with Glyburide Flushing Solution |
|---|---|---|
| Less than 10 (Infusion) | B Braun EXCEL Bag L8000, Carefusion 10010454 administration set with integrated filter | Prepare B Braun EXCEL bag with the required concentration. Flush so that 120 mL is released from the distal end. Wait 15 minutes. Flush tubing with 120 mL of solution. Wait 15 minutes Flush tubing with 120 mL of solution. Wait 15 minutes Attach a newly mixed B Braun EXCEL bag of the same concentration to the administration set, flush with 120 mL of solution immediately prior to administration (i.e. bedside or just before dosing). Each 120 mL flush should take at least approximately 7-8 minutes. |
| 10.0 (Infusion) | Viaflex PVC Bag, Carefusion 2260-0500 administration set plus Cardinal 20350E extension set with filter | Prime so that 10 mL is released from distal end. Wait at least 10 minutes prior to use. Flush with 30 mL immediately prior to administration. |
| All boluses | Standard BD syringe (BD 1 Becton Drive Franklin Lakes, NJ USA 07417) with PALL 0.2 micron filter HP1002 | Flush (the filter) with 21 mL. Expel a further 7 mL. Wait at least 15 minutes before use. Prior to administration, expel 2 mL. |

All components and flushing protocols were extensively tested beforehand to confirm a less than about 10% reduction in glyburide passing through the full chain of components. A glyburide flushing solution has a glyburide concentration of at least about 2 µg/mL, or about 2-8 µs/mL, or about 5-6 µs/mL, or about 10 µg/mL, or greater.

In all cases, the catheter used was a BD Nexiva catheter (BD, 1 Becton Drive, Franklin Lakes, N.J. USA 07417); the catheter was not flushed or tested.

Phase 2 Study

In the treatment of acute diseases, it is not typically desirable to spend time extensively flushing filters and tubing prior to administration, while a patient is awaiting treatment. Thus, since time is often of the essence in clinical situations, such as acute stroke, spinal cord injury, brain trauma, or other brain or nervous system injury or myocardial infarction or ventricular arrhythmias, delaying the administration of a drug to a patient while the pharmacy flushes tubing is not a desirable option. Furthermore, in urgent or emergency situations, it is preferable that a pharmacy have a simple set of instructions to prepare the drug.

Thus, although it may be possible to perform extensive flushing prior to storage of bags and tubing for later use, such a strategy is not preferred, since the stability of glyburide in such a situation has not been determined, and for sterility and other purposes, clinicians may prefer fresh bags and tubing to bags and tubing stored for long periods of time after flushing with glyburide, and pharmacies may prefer to have all its tubing and bags available for use for all drugs, without pre-treatment with glyburide.

We performed preclinical experiments to determine whether it was possible and practical to filter the concentrated reconstituted glyburide material (1 mg/mL) with a 0.2 micron filter (for example the Millex 0.22 um Durapore PVDF filter SLGV033RS or SLGVM33RS (Millipore, 290 Concord Road, Billerica, Mass. 01821), or the PALL 0.2 micron filter, ELP1002) without undue loss of glyburide to the filter. In these experiments, the filtered material was diluted into a PVC-free bag (for example, the B Braun EXCEL L8000). In this protocol, the filtered glyburide solution in the PVC-free bag is ready for administration to a patient through unfiltered polyethylene lined tubing (for example the Carefusion 2260-0500 or Carefusion C20014) or through polyethylene lined tubing that is substantially PVC-free i.e. has only a short section of PVC, for example the Hospira 11993-78 (275 North Field Drive, Lake Forest, Ill. 60045). Note that prior to glyburide administration, the tubing may optionally be flushed with one flush of about 50 mL to about 75 mL (e.g., about 70 mL) of glyburide flushing solution (glyburide concentration of at least about 2 μg/mL, or about 2-8 μg/mL, or about 5-6 μg/mL, or about 10 μg/mL, or greater).

Glyburide has been administered to two patients with such a procedure. In one case, the SLGVM33RS syringe filter and the 2260-0500 administration set with 6×C20014 extension sets attached to it were used. In the other case, the SLGV033RS syringe filter and the Hospira 11993-78 administration set with 6×C20014 extension sets attached to it were used.

Pre-clinical testing shows that this procedure is effective to reduce the loss of glyburide from glyburide solutions.

We found that methods of filtering a glyburide solution that includes a glyburide concentration that is sufficiently high (e.g., at least about 10 μg/mL, preferably between about 0.5 and about 1 mg/mL and even more preferably about 1 mg/mL or greater) so that the filtering process does not significantly decrease the glyburide concentration, and then diluting the solution into a PVC-free bag to provide sufficient volume of solution to allow administration through a standard intravenous (IV) pump, then administering the solution through a filter-less polyethylene lined administration set (or a set that is mostly polyethylene lined with a short PVC section) are effective to provide clinically effective concentrations of glyburide for administration to a patient in need of glyburide treatment. Patients in need of glyburide treatment include patients suffering from stroke, such as acute stroke (ischemic and hemorrhagic), traumatic brain injury (TBI), spinal cord injury (SCI), myocardial infarction (MI), shock (including hemorrhagic shock), organ ischemia, ventricular arrhythmias, ischemic injury; hypoxia/ischemia; and other injuries, conditions, and disorders.

A BD catheter containing BD Vialon™ material was used for both patients (BD, 1 Becton Drive, Franklin Lakes, N.J. USA 07417); the catheter was not flushed or tested.

Pharmacokinetic Data

Healthy volunteers were enrolled into a Phase 1 study of RP-1127 titled "A Phase I Randomized, Double-blind, Placebo-controlled Study to Assess the Safety, Tolerability, and Pharmacokinetics of Escalating Doses of RP-1127 (Glyburide for Injection) in Normal Male and Female Volunteers" (Study 101). The primary objective of this study was to evaluate the safety and tolerability of different dose levels of RP-1127, administered as a bolus dose followed by a 3-day continuous infusion maintenance dose. The secondary objective was to assess the pharmacokinetics and pharmacodynamic responses to RP-1127. Plasma concentrations of glyburide and its two major active metabolites, M1 and M2, were measured.

Five groups of patients were dosed, totaling 26 patients on drug (8 at 17.3 μg bolus plus 0.4 mg/day, 16 at 130 μg bolus plus 3.0 mg/day, 1 at 260 μg bolus plus 6.0 mg/day and 1 at 433 bolus plus 10.0 mg/day) and 8 on placebo. Blood glucose was measured throughout the study, both to obtain pharmacodynamic information as well as for safety reasons. The dosing regimen was a bolus over 2 minutes followed by a continuous infusion for 72 hours.

TABLE 2

Dose Levels in Phase 1

| Bolus Dose (μg) | Hourly Dose (μg/hr) | Day 1 Dose (mg) | Day 2 and Day 3 Doses (mg) | Number of Patients RP-1127 | Placebo | Total |
|---|---|---|---|---|---|---|
| 17.3 | 16.7 | 0.417 | 0.4, 0.4 | 8 | 2 | 10 |
| 130.3 | 125.0 | 3.130 | 3.0, 3.0 | 16 | 4 | 20 |
| 260.0 | 250.0 | 6.260 | 6.0, 6.0 | 1 | 1 | 2 |
| 433.0 | 416.6 | 10.433 | 10.0, 10.0 | 1 | 1 | 2 |
| Total | | | | 26 | 8 | 34 |

All plasma concentration data were analyzed by nonlinear regression, simultaneously incorporating drug behavior during and after the infusion. Results are provided in Table 3

Pharmacokinetic parameters of RP-1127 were independent of dose, weight, height, body surface area, gender and age.

TABLE 3

Pharmacokinetic Parameters of RP-1127 (Glyburide for Injection) from Study 101

| Pharmacokinetic parameters of RP-1127 (Glyburide for Injection) | 0.4 and 3.0 mg/day (N = 26) |
|---|---|
| $T_{1/2\alpha(hr)}$ | 0.44 |
| $T_{1/2\beta(hr)}$ | 3.31 |
| $V_1$ | |
| Liters | 6.0 |
| Liters/kg | 0.088 |
| Liters/m² | 3.36 |
| $V_d$ | |
| Liters | 25.3 |
| Liters/kg | 0.38 |
| Liters/m² | 14.3 |
| Clearance | |
| mL/min | 95 |
| mL/min/kg | 1.44 |
| mL/min/m² | 54 |

As can be seen in Table 2, the pharmacokinetics of RP-1127 were generally consistent with those of other formulations of i.v. glyburide presented in Table 1. However, following the initial bolus loading dose, there was a drop in plasma glyburide concentration, with a minimum reached at a median of 1.25-1.5 hours after commencement of dosing. Plasma glyburide levels increased thereafter, and achieved steady state at approximately 8-20 hours following bolus administration. Steady state was maintained for the remainder of the infusion.

FIG. 1 shows the mean plasma glyburide concentrations measured in patients receiving 0.4 mg/day of glyburide.

The mean steady state glyburide concentration ($C_{ss}$) at 0.4 mg/day was 3.8 ng/mL, and the maximum glyburide concentration ($C_{max}$) was 7.2 ng/mL, which occurred at hour 72. Within one hour of treatment cessation mean glyburide plasma levels were reduced by 54% (from 4.4 ng/mL to 2.0 ng/mL). Glyburide plasma levels for 50% of the patients were below the limits of detection (0.5 ng/mL) by hour 76 and in 100% of patients by hour 96.

Figure 2:
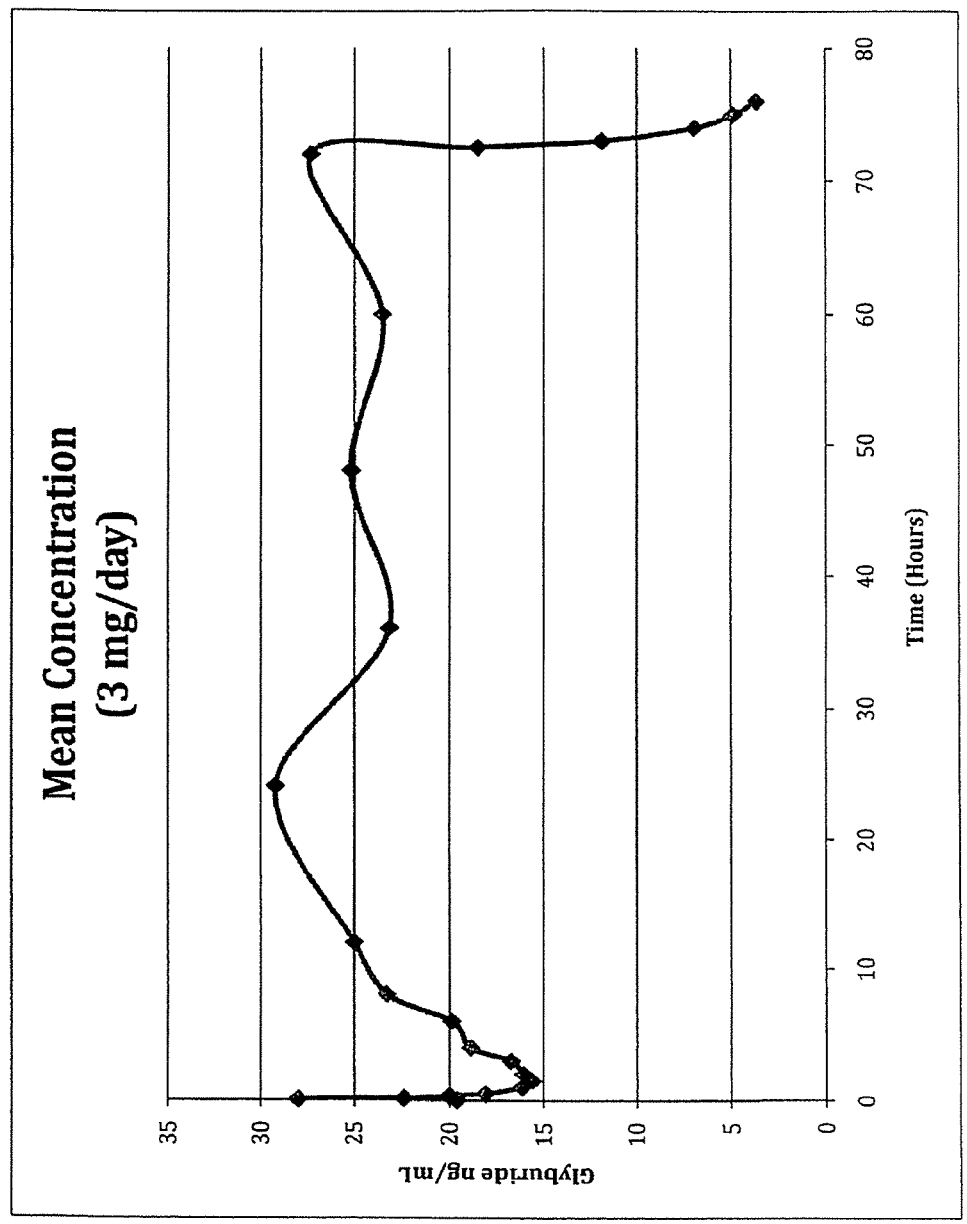
FIG. 2—Mean plasma glyburide concentrations for 3 mg/day glyburide.

FIG. 2 shows the mean plasma glyburide concentrations measured in patients receiving 3 mg/day of glyburide.

For the 3 mg/day dose, mean $C_{ss}$ was 25.3 ng/mL and $C_{max}$ (of all individual subjects) was 50.7 ng/mL, which occurred in one patient at hour 48. Within 1 hour of cessation of dosing, mean glyburide plasma levels were reduced by 57% (from 27.3 ng/mL to 11.9 ng/mL). Glyburide plasma levels were below the limits of detection in 50% of the subjects by hour 84 and in 100% of patients by hour 96.

Figure 3:
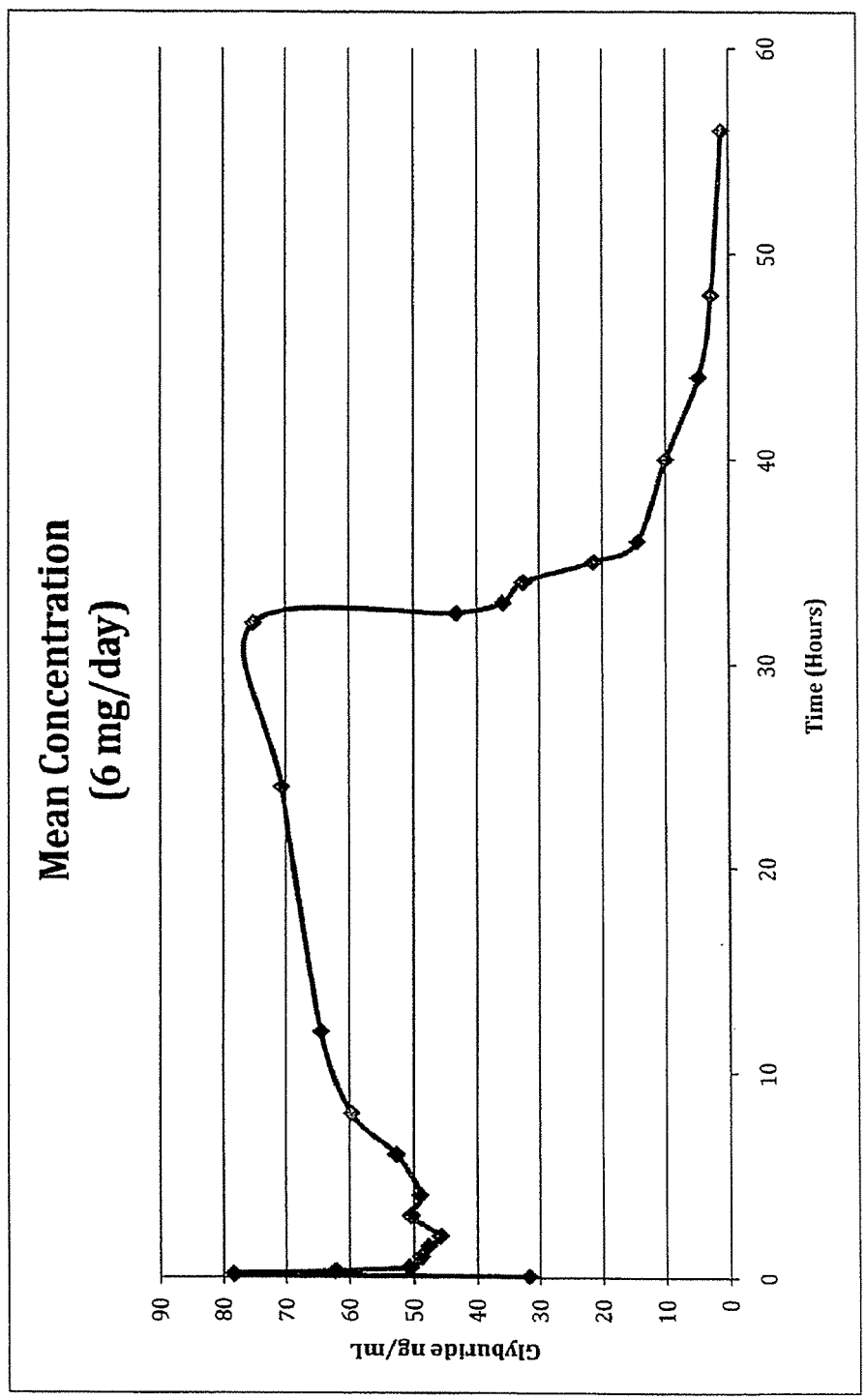
FIG. 3—Mean plasma glyburide concentrations for 6 mg/day glyburide.

FIG. 3 shows the mean plasma glyburide concentrations measured in patients receiving 6 mg/day of glyburide. Dosing was stopped early, at around 32 hours due to the hypoglycemic effect of the drug.

Figure 4:
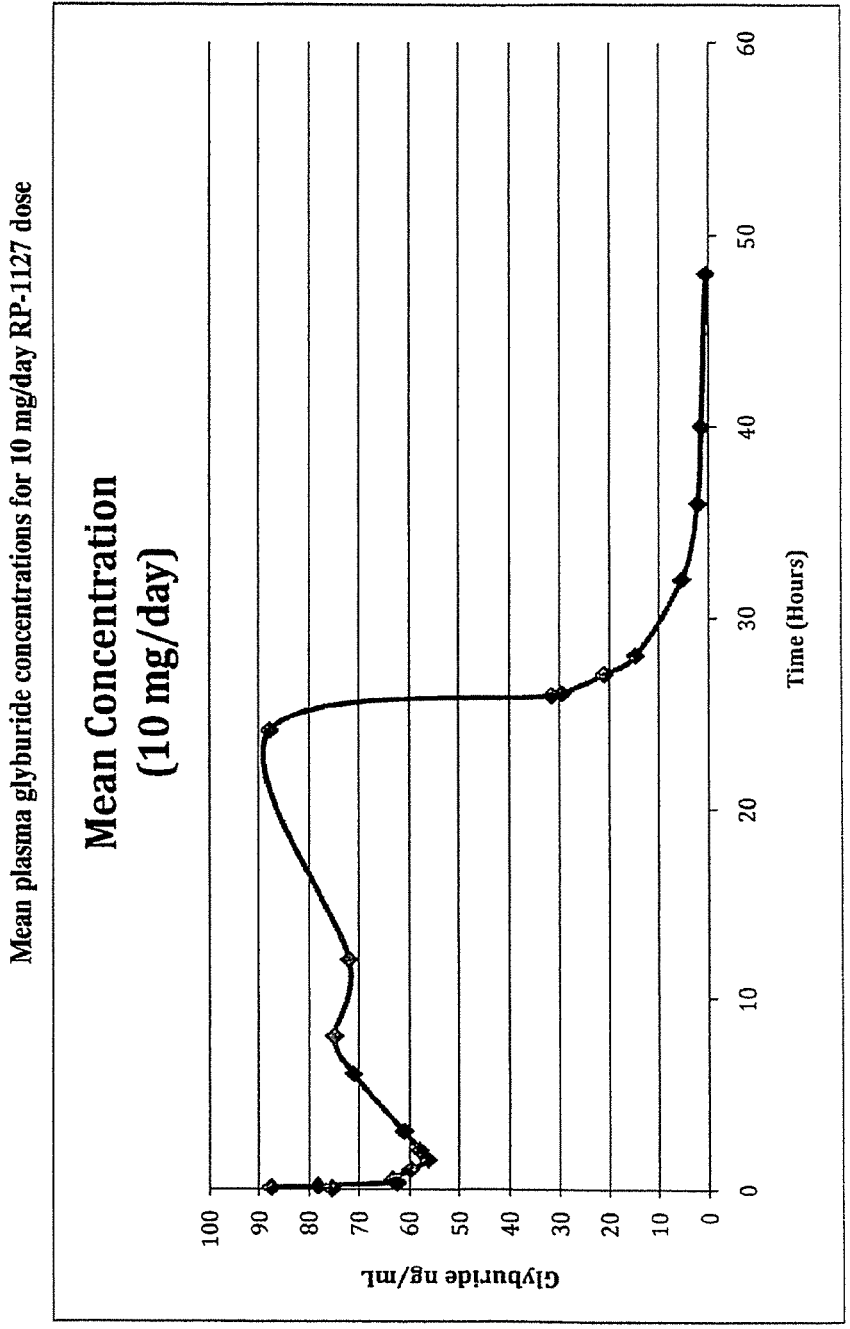
FIG. 4—Mean plasma glyburide concentrations for 10 mg/day glyburide.

FIG. 4 shows the mean plasma glyburide concentrations measured in patients receiving 10 mg/day of glyburide. Dosing was stopped early, at around 24 hours due to the hypoglycemic effect of the drug.

Blood Glucose/Hypoglycemia Data

Figure 5:
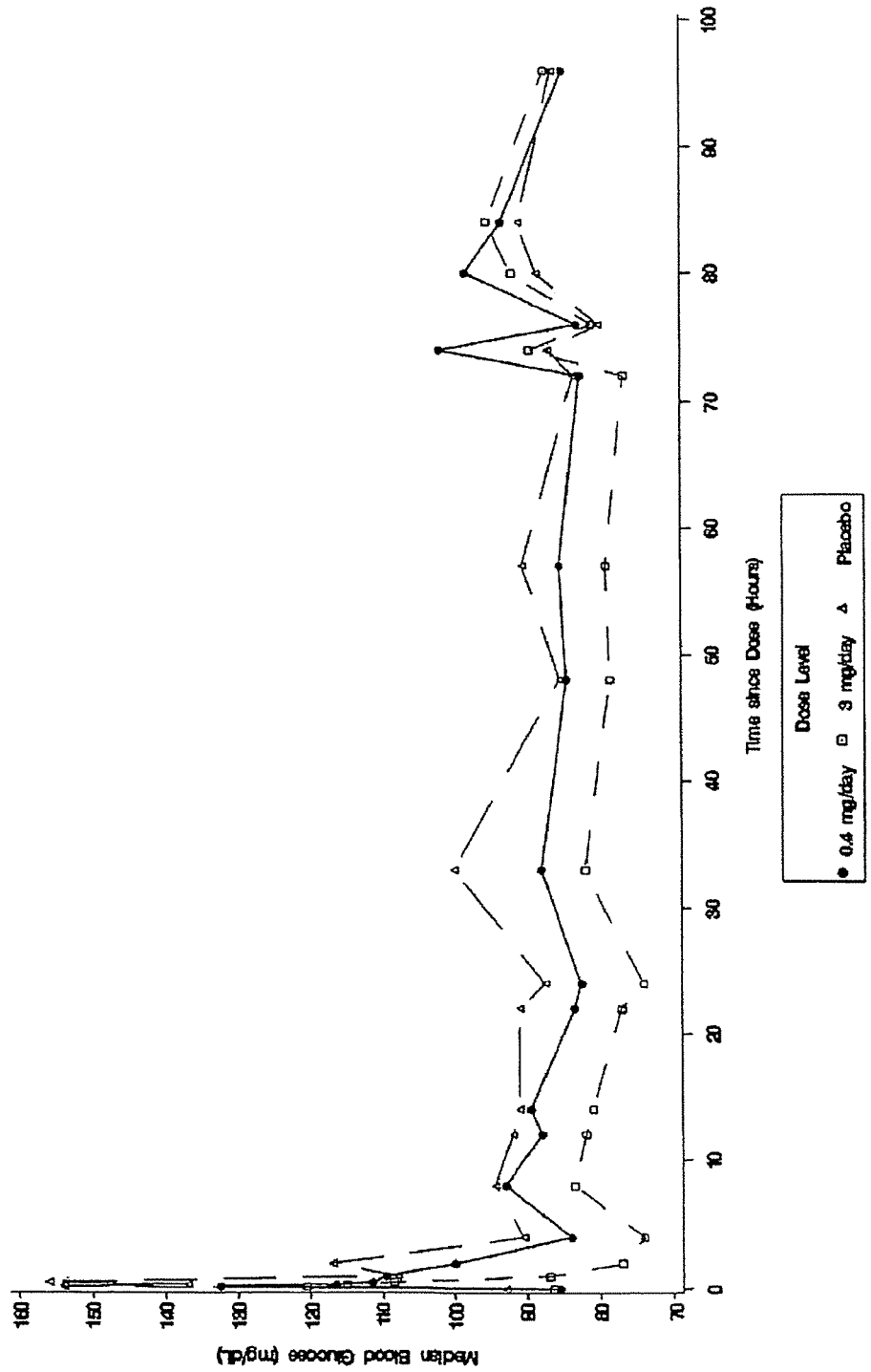
FIG. 5—Median blood glucose levels for placebo (0 mg/day glyburide), 0.4 mg/day glyburide, and 3 mg/day glyburide.

FIG. 5 shows the median blood glucose levels in patients receiving placebo (no glyburide), 0.4 mg/day glyburide, and 3 mg/day glyburide. As can be seen, the 0.4 mg/day dose had a very minor but visible effect on BG and the 3.0 mg/day dose had a more pronounced effect, without hypoglycemia (prolonged BG<70 mg/dL or signs/symptoms of hypoglycemia e.g. shakiness, anxiety, nervousness, palpitations, tachycardia, sweating, feeling of warmth, coldness, clamminess, dilated pupils, feeling of numbness "pins and needles", hunger, nausea, vomiting, abdominal discomfort, headache, impaired judgment, fatigue, weakness, apathy, lethargy, confusion, amnesia, dizziness, delirium, blurred vision, double vision, difficulty speaking, slurred speech, and in more severe cases seizures and coma).

From H0 to H8 the single subject receiving 250 μg bolus plus 6 mg/day of intravenous glyburide experienced a gradual lowering of blood glucose levels, however these remained above 70 mg/dL. Between approximately H8 and H12, blood glucose levels dropped lower, and ranged from 59 to 72 mg/dL. At approximately H13.3, the Subject intermittently displayed signs of hypoglycemia in the form of sweating (diaphoresis) and hunger. These symptoms lasted 15 minutes. Blood glucose measurements at H14 and H15 were within normal ranges, however from approximately H16 to H29 blood glucose fluctuated between 49 and 134 mg/dL. During this period the subject was treated with food PRN but experienced intermittent symptoms of hypoglycemia and at times felt shaky, lightheaded with tunnel vision, and clammy. Subject felt "shaky" and was diaphoretic while eating lunch, and so at approximately H29, the subject was treated with IV dextrose (10%) at a rate of 100 cc/hour, following which blood glucose remained in the range 64-123 mg/dL. Dosing with study drug was suspended at H32 as a result of continued clinical signs of hypoglycemia. The D10 rate was decreased at HR34 to 50 cc/hr and was replaced with IV D5W at approximately HR 36. IV D5W was continued until H48, at which time the patient had been consistently normoglycemic for approximately 7 hours.

Total calories consumed by mouth and IV on day 2 by subject 402 was 4309. The percentage of Kcals: Protein=11%; Carbs=66%; fat=23%.

During this episode, subject had classic symptoms of hypoglycemia but was always alert, oriented and conversant. Subject was also able to consume all food and liquids provided.

Dosing was stopped early, at around 32 hours due to the hypoglycemic effect of the drug.

At H12 the BG was <70 mg/dL (68 mg/dL) and the glyburide plasma level was 64 ng/mL.

The subject receiving 433 μg bolus plus 10 mg/day glyburide experienced blood glucose levels in the range 63 mg/dL-81 mg/dL from HI to H8, which reduced in the 52-53 mg/dL range during HI2-H22. The subject was treated PRN throughout this time with the following: glucose gel, yogurt, apple juice, a bagel and peanut butter. At hour 22, the morning serum glucose below 50 mg/dL at which point dosing was suspended. During this episode, subject had classic symptoms of hypoglycemia but was always alert, oriented and conversant. Subject was also able to consume all food and liquids provided.

Dosing was stopped early, at around 24 hours due to the hypoglycemic effect of the drug.

At hour 2, BG was below 70 mg/dL and the glyburide plasma level was 57.94 ng/mL.

Discussion

Applicant believes that the results disclosed herein provide, for the first time, the results of experiments in which glyburide has been administered for more than a few hours and that plasma levels of glyburide have been recorded. Garrel et al. (1987) administered a 1 mg i.v. bolus dose, followed by 0.3 mg/h for 17 hours, to six subjects with type I diabetes (insulin-dependent diabetes mellitus (IDDM)); the total dose was 6.1 mg glyburide. However, no PK analysis was performed.

Thus, it is believed that no-one has previously observed or described the effects with glyburide described herein.

Applicant notes that severe hypoglycemia occurred at 6 mg/day of glyburide and 10 mg/day of glyburide delivered as continuous infusions (250 μg/hr and 17 μg/hr). It appears that glyburide levels of above about 50 ng/mL, and probably in the range about 58-64 ng/mL or above are sufficient to cause hypoglycemia that is clinically relevant and/or refractory to treatment. It was surprisingly difficult to treat the hypoglycemia caused by the continuous infusion at high doses (6 and 10 mg/day) while maintaining glyburide administration. It is preferred to avoid hypoglycemia, for example, when treating a subject suffering from acute stroke (ischemic and hemorrhagic), traumatic brain injury (TBI), spinal cord injury (SCI), myocardial infarction (MI), shock (including hemorrhagic shock), organ ischemic, and ventricular arrhythmias. Accordingly, plasma levels of glyburide of less than about 50 ng/mL are preferred plasma levels, providing the therapeutic benefits of glyburide while avoiding most or all of the deleterious side effects that higher concentrations might cause (e.g., hypoglycemia). Preferentially, glyburide levels of about 10 ng/mL to about 20 ng/mL, or of about 20 ng/mL to about 30 ng/mL, or of approximately 25 ng/mL should be targeted, it being understood that by doing so, a wide concentration range (up to approximately 50 ng/mL at peak) of glyburide in the blood stream can be expected, at least for short periods of time.

An important point to note is that in acute conditions where intravenous glyburide is likely to be administered e.g. acute stroke (ischemic and hemorrhagic), traumatic brain injury (TBI), spinal cord injury (SCI), myocardial infarction (MI), shock, organ ischemia, and ventricular arrhythmias, the time window during which injury, cell death, or other cell, tissue, or organ damage is maximal is likely to be within about 0-4, or about 0-6, or about 0-12, or about 0-24 hours. Thus attaining the desired glyburide plasma levels quickly is vital. Furthermore in these indications, hypoglycemia can have negative effects, thus it is preferably to treat patients with doses of intravenous glyburide that will not cause extended or clinically significant hypoglycemia.

Furthermore, the difficulty experienced in treating hypoglycemia with oral and iv glucose indicates that the concept of increasing glyburide doses into the hypoglycemic range and then cotreating with glucose may not work. It has been known for some time that carbohydrate "loading" can cause substantial elevations in serum ALT and AST that generally become evident within 1 week of the diet change (Irwi et al 1969, Porikos et al. 1983, Purkins et al. 2003, Kechagieas et al. 2008). Carbohydrate induced aminotransferase elevations are frequently associated with substantial increases in serum triglycerides, probably resulting from increased synthesis of triglyceride in the liver. Deposition of glycogen in hepatocytes is also associated with elevations in serum aminotransferases and this has been described in poorly controlled diabetes (Sayuk et al. 2007, Chatila et al. 1996). Glycogen deposition in the liver could occur quite quickly and may therefore account, at least in part, for aminotransferase elevations observed with carbohydrate loading. It also seems likely that the hyperinsulinemic effect of glyburide would exacerbate the carbohydrate uptake and conversion to glycogen by the liver.

There is evidence from our study outlined in the above rationale i.e. that continued administration of large amount of carbohydrate in parallel to significant increases in insulin release leads to transient elevations in ALT and AST—this was experienced by the subject receiving 6 mg/day glyburide, who was treated with 4,309 calories over 24 hours and two thirds of this was in the form of carbohydrates. This is a very substantial carbohydrate load, far exceeding the daily carbohydrate intake employed in prior healthy volunteer studies that have demonstrated aminotransferase elevations.

While these types of ALT and AST elevations caused by carbohydrate loading are not considered dangerous in normal healthy patients, they are not preferable, especially in labile patients such as ones suffering from acute conditions and should be avoided.

REFERENCES

Bank, A. J., Sih, R., Mullen, K., Osayamwen, M., Lee, P. C. 2000. Vascular ATP-dependent potassium channels, nitric oxide, and human forearm reactive hyperemia. Cardiovasc. Drugs Ther. 14(1):23-29.

Chatila R, West. Hepatomegaly and abnormal liver tests due to glycogenosis in adults with diabetes. Medicine (Baltimore) 75:327-333, 1996.

Garrel, D. R., Picq, R., Bajard, L., Harfouche, M., Tourniaire, J. 1987. Acute effect of glyburide on insulin sensitivity in Type I diabetic patients. J. Clin. Endocrinol. Metab. 65:896-900.

Groop, L., Luzi, L., Melander, A., Groop, P.-H., Ratheiser, K., Simonson, D. C., and DeFronzo, R. A. 1987. Different effects of glyburide and glipizide on insulin secretion and hepatic glucose production in normal and NIDDM subjects. Diabet. 36: 1320-1328.

Groop L C, Barzilai N, Ratheiser K, Luzi L, Wahlin-Boll E, Melander A, DeFronzo R A. Dose-dependent effects of glyburide on insulin secretion and glucose uptake in humans. Diabetes Care. 1991 August; 14(8):724-7.

Irwin M, Staton A J, Dietary wheat starch and sucrose: Effects on levels of 5 enzymes in the blood serum of young adults. Am J Clin Nutr 22, 701-9, 1969.

Jonsson, A., Chan, J. C., Rydberg, T., Vaaler, S., Hallengren, B., Cockram, C. S., Critchley, J. A., and Melander, A. 2000. Pharmacodynamics and pharmacokinetics of intravenous glibenclamide in Caucasian and Chinese patients with type-2 diabetes. Eur. J. Clin. Pharmacol. 55(10):721-727.

Kechagieas S, Emersson A, Dahlqvist O, et al. Fast food based hyper-alimentation can induce rapid and profound elevation in serum alanine aminotransferase in healthy subjects. Gut 35 57(5):649-54, 2008.

McEwen, J., Lawrence, J. R., Ings, R. M. J., Pidgen, A. W., Robinson, J. D., and Walker, S. E. 1982. Characterisation of glibenclamide half-life in man: acute concentration-effect relationships. Clinical Science. 63:28.

Morrison, P. J., Rogers, H. J., and Spector, R. G. 1982. Effect of pirprofen on glibenclamide kinetics and response. Br. J. Clin. Pharmac. 14:123-126.

Neugebauer, G., Betzien, G., Hrstka, V., Kaufmann, B., von Mollendorff, E., Abshagen, U. 1985. Absolute bioavailability and bioequivalence of glibenclamide (Semi-Euglucon N). Int. J. Clin. Pharmacol. Ther. Toxicol. 23(9): 453-60.

Purkins S, Love E R, Eve, M D, et al. The influence of diet upon liver function tests and serum lipids in healthy male volunteers resident in a Phase 1 unit. British Journal of Clinical Pharmacology 57:2, 199-208, 2003.

Porikos K P, Van Italie T B. Diet induced changes in serum transaminase and triglycreride levels in healthy adult men. Am J Med 75:624-30, 1983.

Rydberg, T., Jonsson, A., Roder, M., and Melander, A. 1994. Hypoglycemic activity of glyburide (glibenclamide) metabolites in humans. Diabet. Care. 17:1026-1030.

Rogers, H. J., Spector, R. G., Morrison, P. J., and Bradbrook, J. D. 1982. Pharmacokinetics of intravenous glibenclamide investigated by a high performance liquid chromatographic assay. Diabet. 23:37-40.

Rydberg, T., Jonsson, A., and Melander, A. J. 1995. Comparison of the kinetics of glyburide and its active metabolites in humans. J. Clin. Pharm. Ther. 20(5):283-295.

Sayuk G S, Elwing J E, Lisker-Melman M. Hepatic glycogenosis: An under-recognized source for abnormal liver function tests? Dig Dis Sci. 52:936-938, 2007.

Sorgel, F., Fuhr, U., Kinzig-Schippers, Rusing, G., Zaigler, M., and Staib, A. H. 1997. New Investigation of glibenclamide's bioavailability. Phann. Res. 14:S251.

Spraul, M., Streeck, A., Nieradzik, M., and Berger, M. 1989. Uniform elimination pattern for glibenclamide in healthy Caucasian males. Arzneimittelforschung. 39(11): 1449-1450.

The invention claimed is:

1. A method comprising: filling a container with a glyburide in a concentration of from about 2 μg/mL to about 75 μg/mL, and one or more selected from the group consisting of pharmaceutically acceptable excipients, osmoticants, diluents, buffers, and preservatives;
storing the glyburide in the container, wherein said storing does not reduce the concentration of the glyburide solution stored in the container by more than 10%; and
intravenously administering the glyburide stored in the container to a human subject.

2. The method of claim 1, further comprising attaching tubing to the container.

3. The method of claim 2, wherein the tubing is a polyethylene tubing or a polyethylene-coated tube.

4. The medical device of claim 3, wherein the tubing is a low sorbing polyeythylene-lined tubing.

5. The method of claim 1, further comprising attaching an inline filter to the container.

6. The method of claim 5, wherein the inline filter is a polyethylene inline filter or a polyethylene-coated inline filter.

7. The method of claim 1, wherein the container is a polyethylene bag or a polyethylene-coated bag.

8. The method of claim 1, wherein the glyburide solution comprises glyburide in a concentration of from about 2 μg/mL to about 8 μg/mL.

9. The method of claim 1, wherein the container contains glyburide in sterile water, in saline, in a sugar solution, or a combination thereof.

10. The method of claim 1, wherein about 3 mg/day glyburide is intravenously administered to the human subject.

11. The method of claim 1, comprising intravenously administering glyburide to the human subject such that the human subject acheives a glyburide plasma level of about 10 ng/mL to about 30 ng/mL.

12. The method of claim 1, wherein the human subject has stroke, a spinal cord injury, a brain trauma, a brain injury, a nervous system injury, a myocardial infarction, a ventricular arrhythmia, shock, organ ischemia, hypoxia, ischemia, or a combination thereof.

13. The method of claim 1, wherein the administering step is performed within 12 hours of the human subject suffering stroke, a spinal cord injury, a brain trauma, a brain injury, a nervous system injury, a myocardial infarction, a ventricular arrhythmia, shock, organ ischemia, hypoxia, ischemia, or a combination thereof.

14. The method of claim 1, wherein the human subject has suffered an ischemic stroke.

15. The method of claim 1, wherein the human subject has suffered a hemorrhagic stroke.

16. The method of claim 1, wherein the human subject has suffered a traumatic brain injury (TBI).

17. The method of claim 1, wherein the human subject has hemorrhagic shock.

18. The method of claim 1, wherein the glyburide is intravenously administered for more than 48 hours.

19. The method of claim 1, wherein the glyburide is intravenously administered for more than 72 hours.

20. The method of claim 1, wherein the glyburide is intravenously administered for about 96 hours.

* * * * *